(12) United States Patent
Fitzsimmons et al.

(10) Patent No.: US 7,080,920 B2
(45) Date of Patent: Jul. 25, 2006

(54) ILLUMINATED STORAGE CONTAINER

(76) Inventors: Daniel H. Fitzsimmons, 515 Fenelon Pl., Dubuque, IA (US) 52001; Molly M Fitzsimmons, 515 Fenelon Pl., Dubuque, IA (US) 52001

( * ) Notice: Subject to any disclaimer, the term of this patent is extended or adjusted under 35 U.S.C. 154(b) by 0 days.

(21) Appl. No.: 10/912,201

(22) Filed: Aug. 6, 2004

(65) Prior Publication Data
US 2006/0028820 A1 Feb. 9, 2006

(51) Int. Cl.
*F21V 33/00* (2006.01)
(52) U.S. Cl. ............... 362/155; 362/92; 362/800; 362/802; 62/264
(58) Field of Classification Search ............... 362/154, 362/155, 276, 802, 92, 800; 62/264
See application file for complete search history.

(56) References Cited

U.S. PATENT DOCUMENTS

| 4,754,376 A * | 6/1988 | Winslow ............... 362/154 |
| 6,749,319 B1 * | 6/2004 | Muse ............... 362/154 |
| 6,824,290 B1 * | 11/2004 | Noda et al. ............... 362/155 |

* cited by examiner

*Primary Examiner*—Stephen F Husar
(74) *Attorney, Agent, or Firm*—Michael E. Romani

(57) ABSTRACT

A storage container having a storage tub and lid is described. The lid can be opened for access to an interior region of the tub. A solid-state light source or electro-luminescence is located to illuminate the interior region of the tub in response to an actuated switch contained within the lid. The switch can be gravity actuated. The solid-state light source can emit visible or ultraviolet light wavelengths.

16 Claims, 5 Drawing Sheets

ILLUMINATED STORAGE CONTAINER

FIELD OF THE INVENTION

The present invention relates to storage containers in general and in particular the present invention relates to illuminated storage containers.

BACKGROUND OF THE INVENTION

Top-loading storage containers are used for numerous indoor and outdoor activities. For example, some thermal containers commonly referred to as coolers, include a lid attached to a tub of the container by horizontally mounted hinges. These containers are used in both light and dark environmental conditions, such as food and beverage storage for overnight camping. A problem associated with using these containers in darkness is the inability to see the specific items located within the container. A common option to overcome this problem is to use a hand-held flashlight to view these items. This requires the person searching for items within the container to manipulate those items with just one hand. This presents difficulties in locating the desired item while moving other contents that can be large or slippery, and often submersed in ice water. Additionally, if the person must also hold open the lid of the container, the problem of finding and manipulating items within the storage container increases. Flashlights often utilize a very intense light source that can cause the user to become temporarily blinded once the light source is turned off. This condition is most commonly known as night blindness. Non-portable storage containers, such as a common refrigerator, and some portable storage containers incorporate an incandescent light source to illuminate the interior during usage. These light sources consume large amounts of power making them non-portable or impractical and are easily damaged when subject to shock, vibration and temperature cycles and can leave a user without the benefits of the light source when needed. Additionally, light sources that are separate or detachable, and therefore portable from the storage container, can become misplaced or lost which can leave the user without the benefits of light source when needed.

In addition to illumination, wet conditions in portable coolers often lead to bacteria and unpleasant odors. A common way of removing these odors is to scrub the containers with caustic cleaning products.

There is a need for a portable storage container that addresses some, or all of the above problems.

BRIEF SUMMARY OF THE INVENTION

The present invention addresses deficiencies in the portable storage container. In one embodiment, the interior of a storage container such as portable coolers, tackle boxes, storage areas under seats and the like, is illuminated by an integral light source that automatically illuminates the storage area when an integrally-connected lid is raised from a horizontal to a vertical or near-vertical position. The integral light source allows for "hands free" lighting of the interior of the storage container, eliminating the problem of one-handed manipulation of items contained within the container.

In another embodiment, a storage container comprises a tub having a lid attached to a top region of the tub to allow the lid to be opened for access to an interior region of the tub, and a light source attached to the storage container and located to illuminate the interior region of the tub in response to a gravity-actuated switch coupled to the lid. A power supply is coupled to the light source via the switch, and wherein either the light source, switch or power supply is integrated into the storage container.

In other embodiments, the light source, power source and circuitry is integrally connected to the lid of the storage container. The light source is molded to the underside of the lid of the container in such a position as to afford the greatest amount of illumination. The light source may be of a solid-state light emitting substrate (LED) or electro-luminescence (OLED). The LED, however, offers a wide variety of colors that may reduce night-blindness and will likely outlast the useful life of the storage container. Additionally, the LED requires very little power to operate and thereby possibly allows the battery life to be extended past the useful life of the storage container. The LED is also less subject to damage from shock, vibration and temperature change.

In another embodiment, a storage container comprises a tub having a lid attached to a top region of the tub to allow the lid to be opened for access to an interior region of the tub, and a first light source attached to the storage container and located to illuminate the interior region of the tub, and a second light source attached to the storage container to emit an ultraviolet wavelength in response to user activation of a switch coupled to the lid. A power supply is coupled to the light source via the switch, and wherein either the light source, switch or power supply is integrated into the storage container.

These and other features of the invention will be more apparent from the following detailed description that is provided in connection with the accompanying drawings and illustrated embodiments of the invention.

DETAILED DESCRIPTION OF THE INVENTION

In the following detailed description, reference is made to the accompanying drawings which form a part hereof, an in which is shown by way of illustration specific embodiments in which the invention may be practiced. These embodiments are described in sufficient detail to enable those skilled in the art to practice the invention, and it is to be understood that other embodiments may be utilized, and that structural, logical and electrical changes may be made without departing from the spirit and scope of the present invention Embodiments of the present invention provide an improved lighting device for storage containers which is gravity operated and automatically illuminates the inside of the storage container when a lid is moved from a horizontal to a vertical or near-vertical position. Further, embodiments of the present invention provide a light source that reduces the condition know as night blindness. The present invention can provide a user "hands free" illumination while searching for items contained within a storage container, provide a light source that does not consume large amounts of power, and decrease the possibility of damage to the light source through shock, vibration and temperature cycles.

Figure 1:
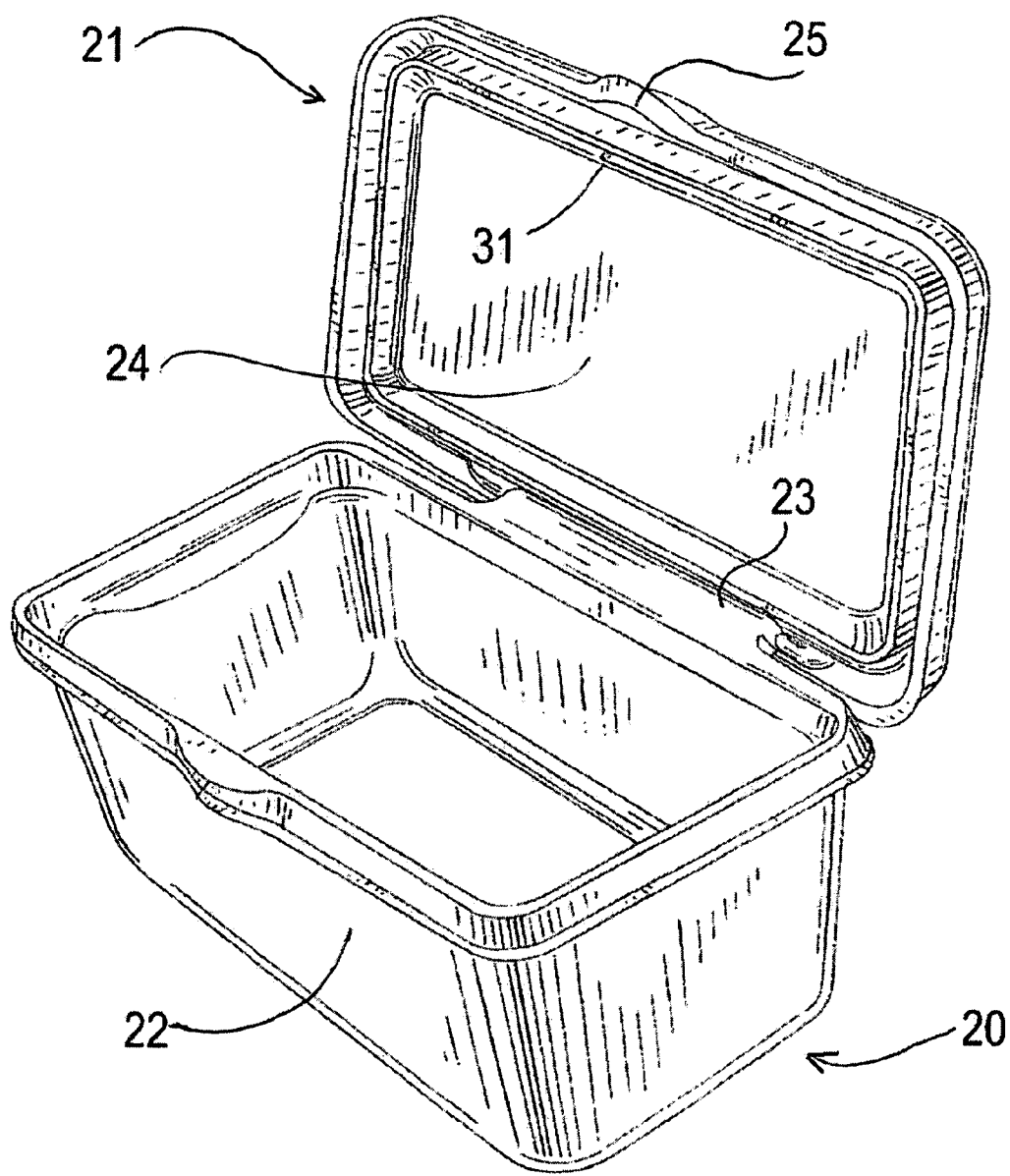
FIG. 1 is a perspective view of the closable portable container in accordance with the invention shown in its "on" position.
Figure 4:
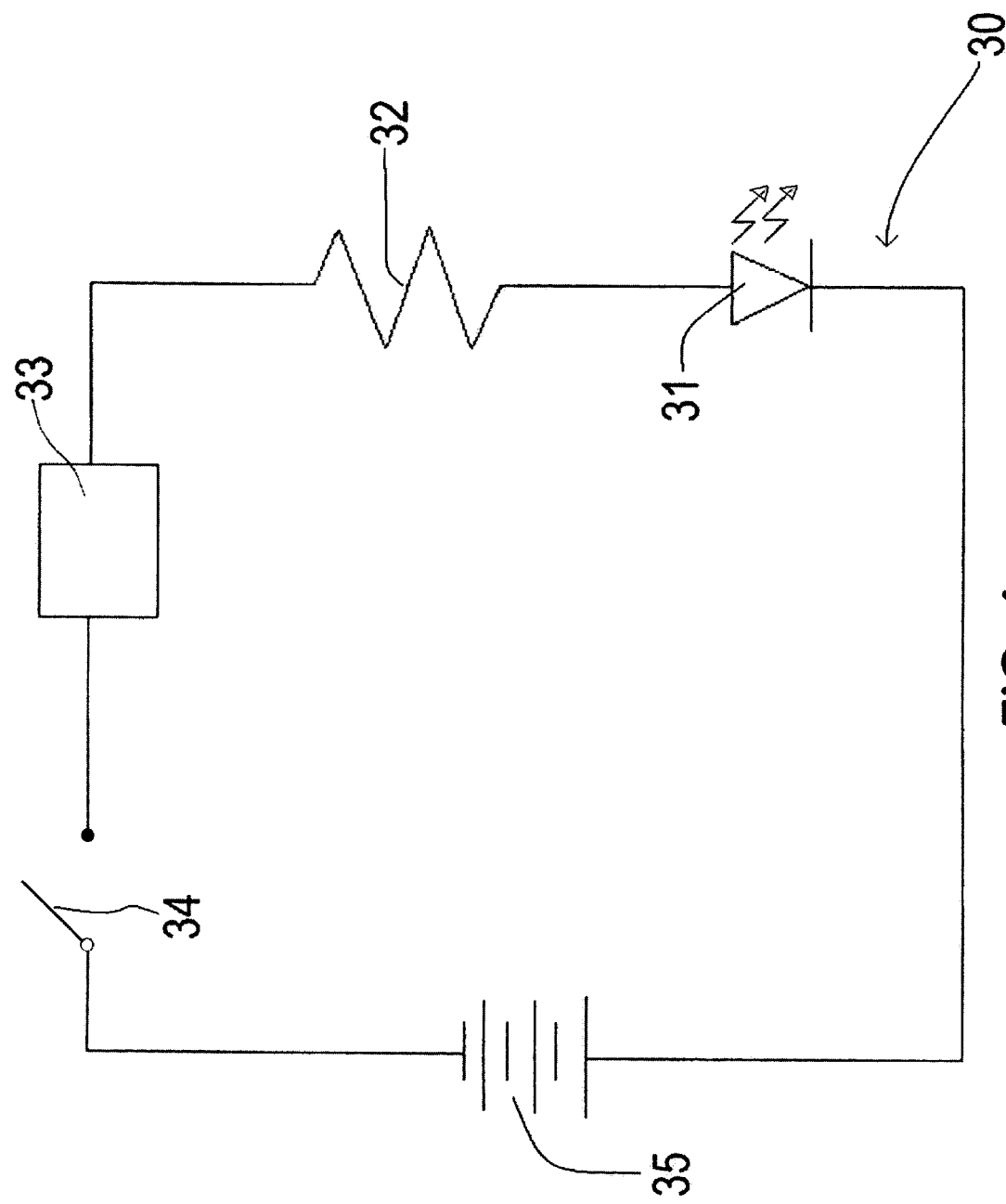
FIG. 4 is a schematic view of the first circuit in accordance with the invention.

Referring now to the drawings the preferred embodiment of this disclosure will be described. A portable storage container with a closable cover is shown generally at 20 in an open or "on" position in accordance with the invention in FIG. 1. Portable storage container 20 has a tub 22 and a cover 21 attached by hinge 23 to tub 22 that may be opened or closed by usually grasping handle 25 and raising or lowering cover 21. When the container is a 'cooler', the tub and lid are typically thermally insulated to isolate the interior storage temperature from exterior environmental conditions. Illumination components making up first circuit 30, FIG. 4, of embodiments of the invention can be contained within the cover of the portable storage container 21. When cover of portable storage container 22 is moved from the horizontal closed or "off" position towards the vertical open or "on" position, switch 34 is closed activating first light source 31. Light 31 may be a solid-state device such as a light emitting substrate (LED) or electro-luminescence. An LED offers a wide variety of light colors and could outlast the useful life of the storage container. Additionally, LED's require little power to operate and thereby possibly allows a power supply battery life to be extended past the useful life of the storage container. The LED is also less subject to damage from shock, vibration and temperature change. Switch 34 in one embodiment is a gravity-activated such as a ball and contact switch. Other types of switches can be incorporated into the circuitry that is operated in response to the position of the container lid.

Figure 2:
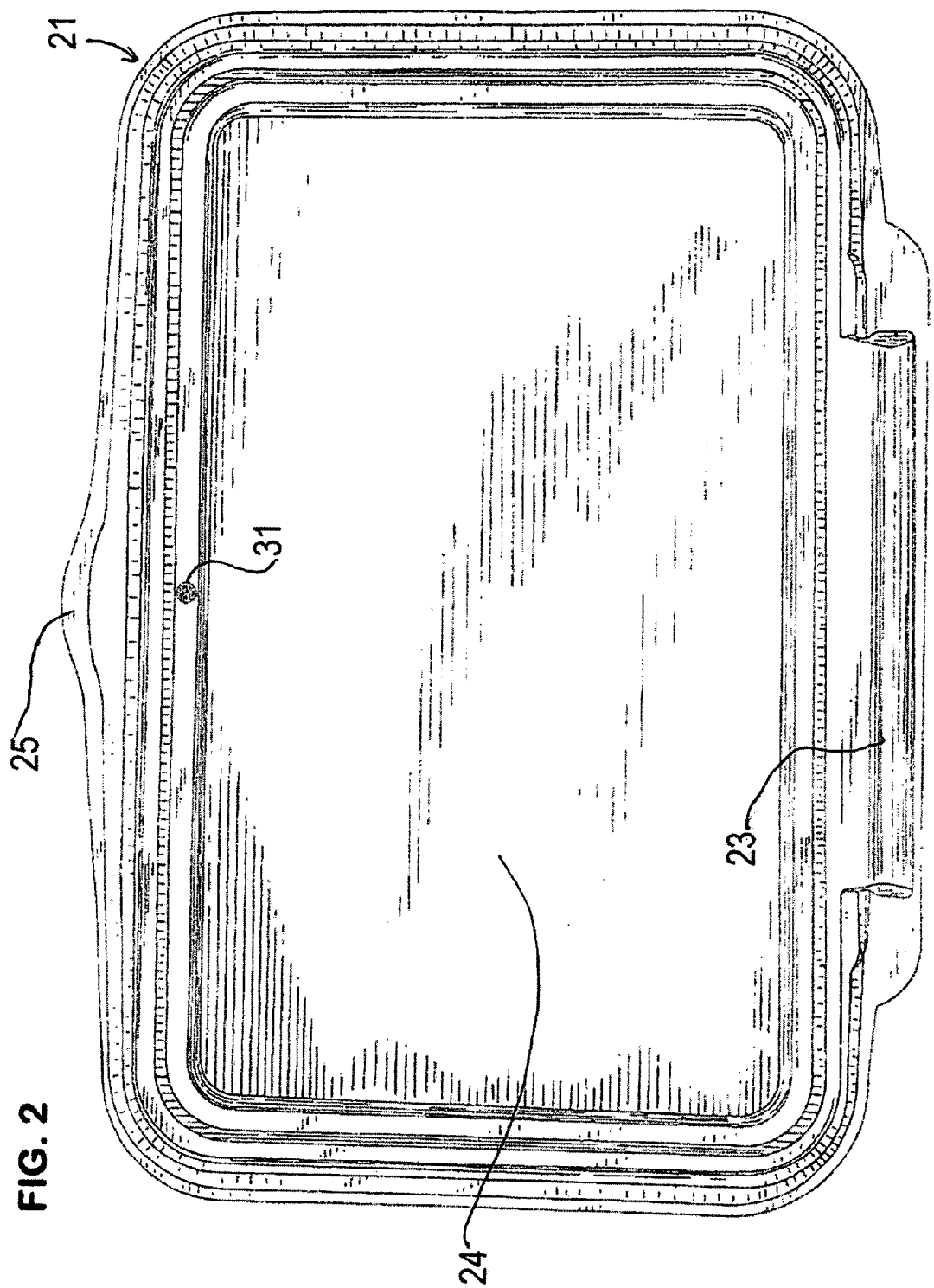
FIG. 2 is a bottom view of the cover of the closable portable container showing the placement of the light source.
Figure 3:
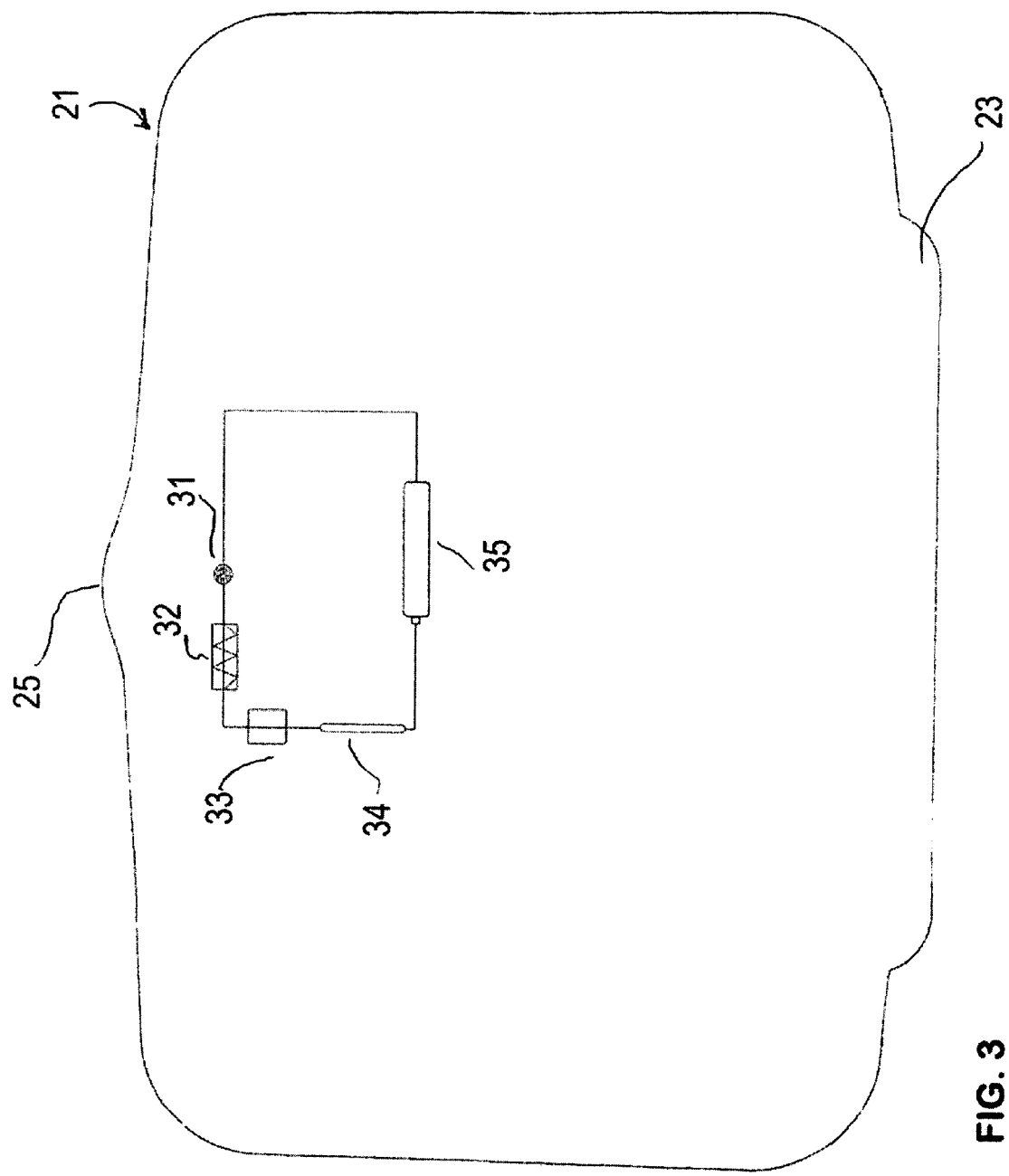
FIG. 3 is a transverse view through the cover of the closable portable container showing the placement of the circuit.

If an optional timer 33 is included in first circuit 30, first light source 31 remains illuminated for a predetermined time period. Referring to FIG. 2, the cover of portable storage container 21 is shown in isolation. In this embodiment, first light source 31 is shown integrally incorporated into the underside of cover 24 towards handle 25 and distant from hinge 23 of the cover of portable storage container 21. It will be understood by those skilled in the art with the benefit of the present detailed description that the light source(s) can be located any place within the container to provide light within the container. The illustrated location is merely one example location. In addition, multiple light sources can be used and the present invention is not limited to one light element. As explained below, an additional light can be added which provides ultraviolet light to combat bacteria growth. Referring now to FIG. 3, illumination circuitry is placed within the cover of the portable storage container 21, with the light source placed in such a way as to minimize damage to the light source 31 during normal operation of the cover. Circuitry placement within the cover is also intended to minimize damage to the circuit during normal usage of the storage container.

Referring again to FIG. 4, there is shown a schematic diagram of a first electrical circuit of one embodiment of the instant invention. First light source 31 is connected to one side of the battery power source 35. Gravity-activated switch 34 is connected between power source 35 and resistor 32 through an optional first one-shot timer 33 Light source 31 is also connected to resistor 32. Light source 31 is a solid-state light source, such as an LED. In operation, switch 34 closes the electrical path through light 31 such that light is provided to the container. The optional one-shot time automatically turns off the light after a predetermined time period to prevent prolonged activation cycles. It will be understood that resistor 32 provides a current limiting feature to protect the light. If additional lights are provided in the circuit the size or need for resistor 32 may change. Although the illustrated embodiment comprises a battery power supply it will be appreciated that an alkaline battery, a rechargeable battery, a DC power supply or an AC power supply could be used with modification of the circuitry where needed.

Figure 5:
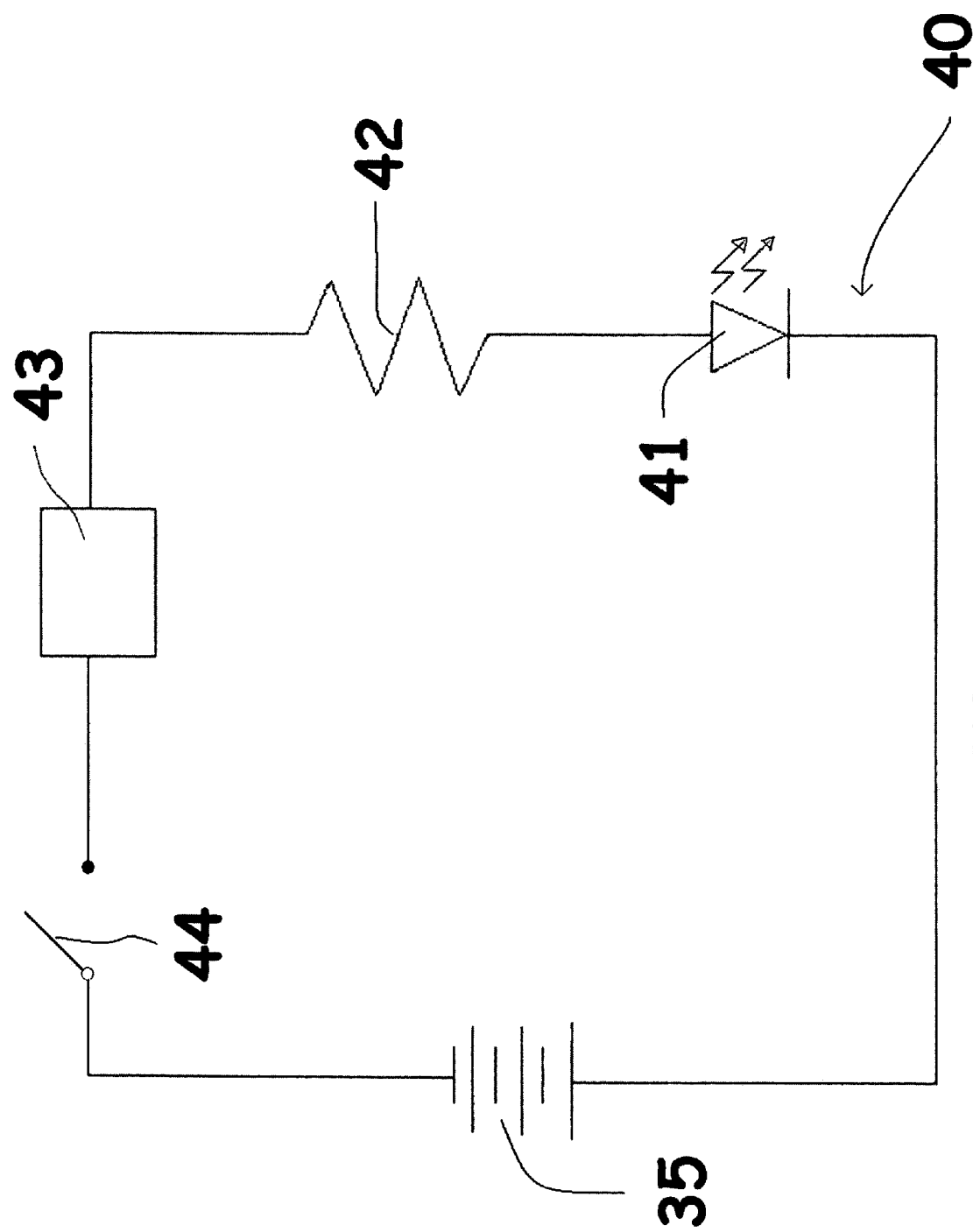
FIG. 5 is a schematic view of the second circuit in accordance with the invention.

Referring now to FIG. 5, there is shown a schematic diagram of a second electrical circuit that can be incorporated in embodiments of the invention. The circuitry of FIG. 5 is substantially the same as the circuit of FIG. 4, with the exception of switch 44 and light 41. In this embodiment light 41 emits ultraviolet light that is used to combat bacterial growth in the container. As such, it is most effective when the container is empty. That is, after food, ice and water have been removed from the container damp conditions often provide an environment for bacterial growth. By activating second circuit 40 a user can flood the interior of the container with ultraviolet light to kill bacteria. Switch 44 can be a user-activated switch to activate light 41 for a predetermined time period. It will be understood that light 41 and light 31 could be implemented into one common circuit. As such, both visible and ultraviolet lights are active at the same time. A user would merely empty the container, activate the circuit and close the container to allow the ultraviolet light to work.

In accordance with embodiments of the invention, activation circuitry can be manufactured separately from the portable storage container 20 and placed into cover 21 in a separate manufacturing step. The integrity of the circuitry can be maintained by then placing a separate permanent or removable cover over the circuitry during manufacturing to environmentally seal the components into the container. If a removable cover is chosen during manufacturing, the end user of the portable storage container 20 may then have access to the circuit at a later time to make repairs in the case of circuit or power source failure. Alternatively, the light and circuitry can be contained within a housing and attached to the interior location of the lid.

In one embodiment having plastic container components, the light source(s) can be molded into the lid or tub of the container in such a position as to afford the greatest amount of illumination. In another embodiment, a light can be placed on the exterior of the container as an indication that the interior light is operating. Further, embodiments of the invention are not limited to portable containers, but could be embodied in other storage devices such as tackle boxes, storage areas under seats and the like. The storage area is illuminated by an integral light source that automatically illuminates the storage area when a lid is raised from a horizontal to a vertical or near-vertical position. The integral light source allows for "hands free" lighting of the interior of the storage container, eliminating the problem of one-handed manipulation of items contained within the container.

The above description and drawings are only to be considered illustrative of exemplary embodiments that achieve the features and advantages of the invention. Although exemplary embodiments of the present invention have been described and illustrated herein, many modifications, even substitutions of materials, can be made without departing from the spirit or scope of the invention. Accordingly, the above description and accompanying drawings are only illustrative of exemplary embodiments that can achieve the features and advantages of the present invention. It is not intended that the invention be limited to the embodiments shown and described in detail herein. The invention is limited only by the scope of the appended claims.

What is claimed is:

1. A storage container comprising;
   a tub having a lid attached to a top region of the tub to allow the lid to be opened for access to an interior region of the tub;
   a solid-state light source located to illuminate the interior region of the tub in response to a gravity actuated switch integrally formed within the lid; and
   a power supply.

2. The storage container of claim 1 wherein the light source is provided in a housing attached to the lid.

3. The storage container of claim 1 wherein the light source emits ultraviolet light when activated.

4. The storage container of claim 1 wherein the-gravity actuated switch is a ball and contact switch integrally formed within the lid.

5. The storage container of claim 1 wherein the tub and lid are thermally insulated to provide a temperature barrier between an interior of the container and external environmental conditions.

6. The storage container of claim 1 further comprising a timer circuit coupled to the light source and power supply to activate the light source for a predetermined time period in response to the switch.

7. A cooler comprising:
   a thermally insulated tub having a thermally insulated lid attached to a top region of the tub to allow the lid to be opened for access to an interior region of the tub;
   a solid state light source located to illuminate the interior region response to a gravity actuated switch integrally formed within the lid; and
   a power supply.

8. The cooler of claim 7 wherein the light source is provided in a housing attached to the lid.

9. The cooler of claim 7 wherein the switch is integrally formed within the lid.

10. The cooler of claim 7 wherein the light source emits ultraviolet light when activated.

11. The cooler of claim 7 further comprising a timer circuit coupled to the light source and power supply to activate the light source for a predetermined time period in response to the switch.

12. A cooler comprising:
    a thermally insulated plastic tub having a thermally insulated plastic lid attached to a top region of the tub to allow the lid to be opened for access to an interior region of the tub;
    a gravity actuated switch environmentally sealed within the lid;
    a power source located within either the lid or tub; and
    a light emitting diode (LED) located to illuminate the interior region of the tub in response to the gravity actuated-switch and the power source.

13. The cooler of claim 12 wherein the LED is integrally formed within either the lid or tub.

14. The cooler of claim 12 wherein the LED source emits ultraviolet light when activated.

15. A cooler comprising:
    a thermally insulated plastic tub having a thermally insulated plastic lid attached to a top region of the tub to allow the lid to be opened for access to an interior region of the tub;
    a gravity actuated switch environmentally sealed within the lid;
    a power source located within either the lid or tub,
    a light emitting diode (LED) located to illuminate the interior region of the tub in response to the gravity actuated-switch and the power source; and an externally visible second light source coupled to be activated when the light emitting diode is activated.

16. A method of reducing bacteria in a thermally insulated container comprising a thermally insulated tub having a thermally insulated lid attached to a top region of the tub to allow the lid to be opened for access to an interior region of the tub, an ultraviolet light source integrally coupled to the container and located to emit an ultraviolet wavelength into the interior region of the tub in response to an activated switch, a timer circuit, and a power supply, the method comprising:
    activating the switch;
    illuminating an interior region of the container for a time period of the timer circuit with an ultraviolet wavelength to kill bacteria.

* * * * *